United States Patent
Ruan et al.

(10) Patent No.: US 12,156,859 B2
(45) Date of Patent: Dec. 3, 2024

(54) METHODS OF AND COMPOSITIONS FOR TREATING OBESITY, OBESITY-RELATED DISEASES OR CANCERS USING A N6-METHYLLYSINE/L-LYSINE MIXTURE

(71) Applicant: Tainnovation Inc, Los Gatos, CA (US)

(72) Inventors: Jhen-Wei Ruan, Tainan (TW); Chih-Cheng Tai, Campbell, CA (US); Cheng-Yuan Kao, Davis, CA (US)

(73) Assignee: Tainnovation Inc., Los Gatos, CA (US)

( * ) Notice: Subject to any disclaimer, the term of this patent is extended or adjusted under 35 U.S.C. 154(b) by 0 days.

(21) Appl. No.: 18/082,723

(22) Filed: Dec. 16, 2022

(65) Prior Publication Data

US 2024/0197662 A1    Jun. 20, 2024

Related U.S. Application Data

(60) Provisional application No. 63/291,620, filed on Dec. 20, 2021.

(51) Int. Cl.
| | |
|---|---|
| *A61K 31/198* | (2006.01) |
| *A61K 35/741* | (2015.01) |
| *A61K 35/742* | (2015.01) |
| *A61K 35/744* | (2015.01) |
| *A61K 35/745* | (2015.01) |
| *A61K 35/747* | (2015.01) |
| *A61K 47/26* | (2006.01) |
| *A61P 3/04* | (2006.01) |

(52) U.S. Cl.
CPC .......... *A61K 31/198* (2013.01); *A61K 35/741* (2013.01); *A61K 35/742* (2013.01); *A61K 35/744* (2013.01); *A61K 35/745* (2013.01); *A61K 35/747* (2013.01); *A61K 47/26* (2013.01); *A61P 3/04* (2018.01)

(58) Field of Classification Search
None
See application file for complete search history.

(56) References Cited

U.S. PATENT DOCUMENTS

| | | | |
|---|---|---|---|
| 10,960,030 B2 | 3/2021 | Kao | |
| 2014/0079676 A1* | 3/2014 | Olmstead | A61K 9/0053 424/93.45 |
| 2018/0255821 A1* | 9/2018 | Vincent | A23P 10/30 |
| 2019/0358176 A1* | 11/2019 | Vogt | A61P 35/00 |

FOREIGN PATENT DOCUMENTS

| | | | | |
|---|---|---|---|---|
| WO | 2010105207 A1 | 9/2010 | | |
| WO | 2016033439 A2 | 3/2016 | | |
| WO | 2016110585 A1 | 7/2016 | | |
| WO | WO-2017042347 A1 * | 3/2017 | .......... | A23L 33/105 |
| WO | 2017180987 | 10/2017 | | |
| WO | WO-2020037076 A1 * | 2/2020 | .......... | A61K 31/138 |

OTHER PUBLICATIONS

Minelli & Benini (2008) Relationship between number of bacteria and their probiotic effects, Microbial Ecology in Health and Disease, 20:4, 180-183, DOI: 10.1080/08910600802408095 (Year: 2008).*

Liu, R., Hong, J., Xu, X. et al. Gut microbiome and serum metabolome alterations in obesity and after weight-loss intervention. Nat Med 23, 859-868 (2017). https://doi.org/10.1038/nm.4358 (Year: 2017).*

Baskal S, et al. Profile of urinary amino acids and their posttranslational modifications (PTM) including advanced glycation end-products (AGEs) of lysine, arginine and cysteine in lean and obese ZSF1 rats. Amino Acids. Apr. 2022 (online Jul. 2021);54(4):643-652. doi: 10.1007/s00726-021-03042-3 (Year: 2021).*

Seale, P. & Lazar, M. A. Brown fat in humans: turning up the heat on obesity. Diabetes 58, 1482-1484, doi: 10.2337/db09-0622 (2009).

Bartelt, A. & Heeren, J. Adipose tissue browning and metabolic health. Nat Rev Endocrinol 10, 24-36, doi:10.1038/prendo.2013.204 (2014).

Arner, P. & Ryden, M. Human white adipose tissue: A highly dynamic metabolic organ. J Intern Med, doi:10.1111/oim.13435 (2021).

Kalinovich, A. V., de Jong, J. M., Cannon, B. & Nedergaard, J. UCP1 in adipose tissues: two steps to full browning. Biochimie 134, 127-137, doi:10.1016/j.biochi.2017.01.007 (2017).

Nedergaard, J. & Cannon, B. The browning of white adipose tissue: some burning issues. Cell Metab 20, 396-407, doi:10.1016/j.cmet.2014.07.005 (2014).

Li, G. et al. Intermittent Fasting Promotes White Adipose Browning and Decreases Obesity by Shaping the Gut Microbiota. Cell Metab 26, 672-685 e674, doi:10.1016/j.cmet.2017.08.019 (2017).

Chevalier, C. et al. Gut Microbiota Orchestrates Energy Homeostasis during Cold. Cell 163, 1360-1374, doi:10.1016/j.cell.2015.11.004 (2015).

Suarez-Zamorano, N. et al. Microbiota depletion promotes browning of white adipose tissue and reduces obesity. Nat Med 21, 1497-1501, doi: 10.1038/nm.3994 (2015).

Lin, R., Liu, W., Piao, M. & Zhu, H. A review of the relationship between the gut microbiota and amino acid metabolism. Amino Acids 49, 2083-2090, doi: 10.1007/s00726-017-2493-3 (2017).

Zhao-Lai Dai, G. W., Wei-Yun Zhu. Amino acid metabolism in intestinal bacteria: links between gut ecology and host health. Front. Biosci. 16, 1768-1786 (2011).

(Continued)

*Primary Examiner* — J. E. Angell
*Assistant Examiner* — Kathryn A Smith
(74) *Attorney, Agent, or Firm* — Haverstock & Owens, A Law Corporation

(57) ABSTRACT

The present disclosure relates to utilizing the N6-methyllysine for reducing fat percentage in an organ or tissue or for treating obesity, obesity-related diseases or cancers. More specifically, the present invention relates to the method using Nε-Methyl-L-lysine or Nε-Methyl-L-lysine producing bacteria or Nε-Methyl-L-lysine/l-lysine mixture or Nε-Methyl-L-lysine/probiotics mixture to treat obesity, obesity-related diseases or cancers.

6 Claims, 17 Drawing Sheets

(56) References Cited

OTHER PUBLICATIONS

Matthews, D. E. Review of Lysine Metabolism with a Focus on Humans. J. Nutr. 150, 2548S-2555S, doi: 10.1093/jn/nxaa224 (2020).
Cedar, H. & Bergman, Y. Linking DNA methylation and histone modificatio; patterns and aparadigms. Nat Rev Genet 10, 295-304, doi: 10.1038/nrg2540 (2009).n.
Huszar, G., Elzinga, M. ε-N-Methyl Lysine in Myosin. Nature 223, 834-835 (1969).
Ann Stock, S. C., Catherine Clarke and Jeff Stock N terminal methylation of proteins Structure function and specificity. FEBS Lett. 220, 8-14 (1987).
Ambler, R., Rees, M. ε-N-Methyl-lysine in Bacterial Flagellar Protein. Nature 184, 56-57 (1959).
Perry, T., Diamond, S. & Hansen, S. ε-N-Methyl Lysine: an Additional Amino-acid in Human Plasma. Nature 222, 668 (1969).
Chen, H. F., Chuang, H. C. & Tan, T. H. Regulation of Dual-Specificity Phosphatase (DUSP) Ubiquitination and Protein Stability. Int J Mol Sci 20, doi: 10.3390/ijms20112668 (2019).
An, N. et al. Dual-specificity phosphatases in mental and neurological disorders. Prog Neurobiol 198, 101906, doi:10.1016/j.pneurobio.2020.101906 (2021).
Zhang, B. et al. DUSP6 expression is associated with osteoporosis through the regulation of osteoclast differentiation via ERK2/Smad2 signaling. Cell Death Dis 12, 825, doi:10.1038/s41419-021-04110-y (2021).
Tsai, H. Y. et al. Inhibition of DUSP6 Activates Autophagy and Rescues the Retinal Pigment Epithelium in Sodium Iodate-Induced Retinal Degeneration Models In Vivo and In Vitro. Biomedicines 10, doi:10.3390/biomedicines 10010159 (2022).
Ahmad, M. K., Abdollah, N. A., Shafie, N. H., Yusof, N. M. & Razak, S. R. A. Dual-specificity phosphatase 6 (DUSP6): a review of its molecular characteristics and clinical relevance in cancer. Cancer Biol Med 15, 14-28, doi:10.20892/j.issn.2095-3941.2017. 0107 (2018).
Wu, Z. et al. MAPK phosphatase-3 promotes hepatic gluconeogenesis through dephosphorylation of forkhead box O1 in mice. J Clin Invest 120, 3901-3911, doi: 10.1172/JCI43250 (2010).
Ruan, J. W. et al. Dual-specificity phosphatase 6 deficiency regulates gut microbiome and transcriptome response against diet-induced obesity in mice. Nat Microbiol 2, 16220, doi:10.1038/nmicrobiol.2016.220 (2016).
Sonnenburg, J. L. & Backhed, F. Diet-microbiota interactions as moderators of human metabolism. Nature 535, 56-64, doi:10.1038/nature18846 (2016).
The International Search Report and Written Opinion from PCT Patent Application No. PCT/US2022/053110 dated Mar. 30, 2023.
Liu et al., Intervening Effects of Total Alkalolds of Corydalis saxicola Bunting on Rats With Antibiotic-Induced Gut Microbiota Dysbiosis Based on 16S rRNA Gene Sequencing and Untargeted Metabolomics Analyses, Frontiers in Microbiology, May 31, 2019, vol. 10 Article No. 1151, pp. 1-18 Entire document.
Reis et al. Influence of Formaldehyde-treated casein supplements on the concentration of epsition-N-methyllysine in sheep plasma, Australian Journal of Biological Sciences, 1973, vol. 26, No. 5 pp. 1127-1136. Entire document.
The International Preliminary Report from PCT Patent Application No. PCT/US2022/053110 dated Jul. 4, 2024.

\* cited by examiner

METHODS OF AND COMPOSITIONS FOR TREATING OBESITY, OBESITY-RELATED DISEASES OR CANCERS USING A N6-METHYLLYSINE/L-LYSINE MIXTURE

FIELD

The present disclosure relates to utilizing the N6-methyllysine for treating obesity, obesity-related diseases or cancers. More specifically, the present disclosure relates to the method using Nε-Methyl-L-lysine, Nε-Methyl-L-lysine producing bacteria, Nε-Methyl-L-lysine/l-lysine mixture, or Nε-Methyl-L-lysine/probiotics mixture to treat obesity, obesity-related diseases or cancers.

BACKGROUND

Obesity is now a plague in developed countries as well as in many developing countries. Since obesity increases the risk of many health conditions, including cardiovascular disease, stroke, type 2 diabetes, fatty liver and certain cancers, it is important to understand the detailed mechanism of obesity development and search for novel ways to treat obesity.

Gut microbiome plays a critical role in regulating human physiology. The plasticity is important for a gut microbiome to prevent entering the dysbiosis state that is associated with the development of numerous human diseases. To regulate the functions of different organs, a gut microbiome can produce varies bacterial metabolites like short-chain fatty acids, amino acids and chemicals for modulating specific biological processes in the host. When engaging in particular environmental challenges, like fasting or coldness, the gut microbiome is essential for regulating adipose function to maintain energy homeostasis. Recently, fasting has been suggested to be a potential therapy for various diseases, including metabolic disorders and cancers. Fasting has been shown to change the composition of microbiota for regulating adipose browning. However, the specific metabolites derived from fasting-adapted microbiota regulating host physiology remain unclear.

According to this, finding a method for treating obesity with controlling gut microbiome may be a possible way.

SUMMARY

To achieve the above-mentioned purpose, the present disclosure provides a method for treating obesity, obesity-related diseases or solid tumors comprising:
a. diagnosing a subject in need of treatment for obesity, obesity-related diseases or cancers;
b. increasing either the amount of or the activity of a Nε-Methyl-L-lysine in the subject; and
c. optionally increasing the amount the Nε-Methyl-L-lysine producing bacteria in the gut of the subject.

In other embodiments, the present disclosure provides a method for adjusting bodily fat comprising:
a. determining a subject in need of adjustment of bodily fat percentage, location, or amount;
b. increasing either the amount of or the activity of a Nε-Methyl-L-lysine in the subject; and
c. optionally increasing the amount of the Nε-Methyl-L-lysine producing bacteria in the gut of the subject.

In some other embodiments, the present disclosure provides a method for adjusting bodily fat comprising:
a. determining a subject in need of adjustment of bodily fat percentage, location, or amount;
b. increasing either the amount of or the activity of a Nε-Methyl-L-lysine in the subject; and
c. optionally increasing/increasing the amount of the Nε-Methyl-L-lysine producing bacteria in the gut of the subject.

In some embodiments, the obesity-related diseases is selected from the group consisting of metabolic syndrome, type II diabetes, hypertension, cardiovascular disease, nonalcoholic fatty liver disease, nonalcoholic steatohepatitis, liver fibrosis and liver cirrhosis.

In some embodiments, the amount of Nε-Methyl-L-lysine is increased in the subject by administering an effective amount of Nε-Methyl-L-lysine or Nε-Methyl-L-lysine hydrochloride or N(6)-Methyllysine producing bacteria to the subject. In some embodiments, the Nε-Methyl-L-lysine is synthetically produced in a lab. In some embodiments, the Nε-Methyl-L-lysine is higher in an amount or density than any naturally occurred amount in an animal or human body.

In some embodiments, the subject is selected from the group consisting of a human, a dog, a cat, a cow, a horse, a rabbit, a pig, a goat, an avian species and a fish species.

In some embodiments, the amount of or the activity of the Nε-Methyl-L-lysine is increased by administration of a DUSP6 antagonist to the subject.

In some embodiments, the method further comprising performing a chemotherapy or an immunotherapy of cancers on the subject by administering an effective amount of Nε-Methyl-L-lysine or Nε-Methyl-L-lysine producing bacteria to the subject. In some embodiments, the method further comprising performing a non-medical treatments but just a dietary or a cosmetic adjustment.

In some embodiments, the present application is to provide a method for decreasing body fat or for promoting weight loss in a subject comprising: increasing either the amount of or the activity of a Nε-Methyl-L-lysine in the subject.

In some embodiments, the present application is to provide a method for altering the microbiota composition in the subject's gastrointestinal tract comprising: administering an effective amount of Nε-Methyl-L-lysine or Nε-Methyl-L-lysine hydrochloride or Nε-Methyl-L-lysine producing bacteria.

In some embodiments, the method further comprising increasing the number of total gut bacteria and the bacteria classified in the Actinobacteria phylum, Bacteroidia phylum, Verrucomicrobiota phylum, Bacilli class Coriobacteriia class, Saccharimonadia class, *Bifidobacterium* genus, and *Lactobacillus* genus.

In some embodiments, the method further comprising increasing the amount of *Akkernmansia muciniphilla*.

In some embodiments, the present application is to provide a method for manufacturing food supplement for treating obesity, obesity-related diseases or cancers, comprising: preparing a mixture of Nε-Methyl-L-lysine; and adding said mixture into food.

In some embodiments, the amount of Nε-Methyl-L-lysine is an effective amount of Nε-Methyl-L-lysine/L-lysine mixture to the subject.

Still in some embodiments, the present application is to provide a method for manufacturing probiotic composition for treating obesity, obesity-related diseases or cancers, comprising: preparing a mixture of Nε-Methyl-L-lysine, and adding said mixture into probiotic.

In some embodiments, the probiotic is selected from the group consisting of *Akkermansia muciniphila, Bifidobacterium bifidum, Bifidobacterium breve, Bifidobacterium longum* subsp. *infantis, Bifidobacterium longum, Lactoba-* cillus acidophilus, Lactobacillus casei, Lactococcus lactis, Lactobacillus casei subsp. paracasei, Lactobacillus plantarum, Lactobacillus rhamnosus*, and *Streptococcus thermophilus*.

In some embodiments, the present application is to provide a method of for regulating gut microbiota in a subject comprising: increasing either the amount of or the activity of a Nε-Methyl-L-lysine in the subject.

In some embodiments, the present application is to provide a method of counteracting cancer-related immune suppression and restore effective antitumor immunity, comprising administering one or more of compositions including Nε-Methyl-L-lysine.

In some embodiments, the present application is to provide a method of improving cancer survival rates, and quality of life, comprising administering one or more of compositions including Nε-Methyl-L-lysine.

In some embodiments, the present application is to provide a dietary supplement formulation comprising: a) a mixture of one or more active ingredients and one or more fillers, wherein the one or more active ingredients contain at least 105 CFU of a Nε-Methyl-L-lysine, Nε-Methyl-L-lysine hydrochloride, or Nε-Methyl-L-lysine producing bacteria; and b) a package enclosing the mixture.

In some embodiments, the mixture is packed in multiple edible containers. The edible containers comprise capsules, tablets, granules, particles or powders.

In some embodiments, the mixture comprises an amount of prebiotic. The prebiotic comprises Inulin, Fructo-Oligosaccharide (FOS), Galacto-oligosaccharides (GOS), or amino acids.

With the above-mentioned technical features, the provided method treats obesity by controlling the amount of or the activity of a Nε-Methyl-L-lysine, or by controlling the gut bacteria. As such, the obesity-related diseases or solid tumors may also be benefited.

BRIEF DESCRIPTION OF THE DRAWINGS

Embodiments will now be described by way of examples, with reference to the accompanying drawings which are meant to be exemplary and not limiting. For all Figures mentioned herein, like numbered elements refer to like elements throughout.

FIGS. 3A-3L illustrates some other experimental results in accordance with some embodiments. (A) of FIG. 3A shows Liquid chromatography tandem mass spectrometry (LC-MS/MS) fragmentation of Nε-Methyl-L-lysine. (B) of FIG. 3B shows Bodyweight of chow diet-fed male mice orally administrated with Vehicle (H$_2$O), L-lysine or Nε-Methyl-L-lysine for fourteen days. N=6-8 mice of each group. (C-D) of FIGS. 3E and 3F show analyses of average adipocyte area (C) and adipocyte size distribution (D) were performed by Adiposoft software on histological pWAT sections stained with H&E of vehicle- and Nε-Methyl-L-lysine treated mice. (E-F) of FIGS. 3G and 3H show analyses of average adipocyte area (E) and adipocyte size distribution (F) were performed by Adiposoft software on histological iWAT sections stained with H&E of vehicle- and Nε-Methyl-L-lysine treated mice. (G) of FIG. 3I shows the experimental scheme of mouse CDAHFD-induced NASH model. (H) of FIG. 3J shows quantification of lipid droplets area was performed by ImageJ software on histological liver sections stained with H&E of CDAHFD fed mice treated with the vehicle, L-lysine, and Nε-Methyl-L-lysine. (I-J) of FIGS. 3I and 3J show quantification of fibrotic collagen area was performed by ImageJ software on histological liver sections stained with masson's trichrome stain of CDAHFD fed mice treated with the vehicle, L-lysine, and Nε-Methyl-L-lysine. N=8 mice of each group. Data are presented as mean±SEM. ns, statistically non-significant; *P<0.05; P<0.01; *P<0.001; ****P<0.0001 according to Mann-Whitney tests and One-Way ANOVA analysis with Tukey post-hoc test. No collected data were excluded for analysis.

DETAILED DESCRIPTION OF THE PREFERRED EMBODIMENT

Figure 1A:
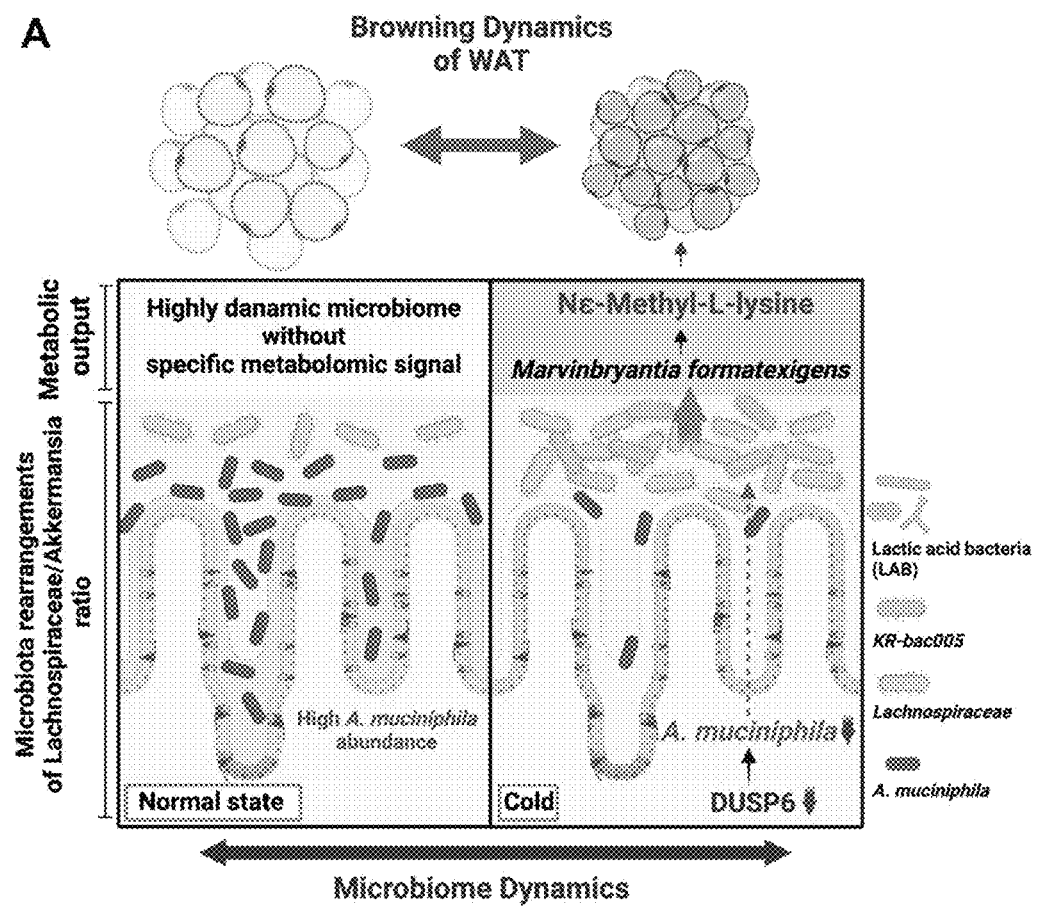
FIG. 1A illustrates microbiome dynamics between normal state and cold stress or fasting stress.

Reference is made in detail to the embodiments of the present disclosure, examples of which are illustrated in the accompanying drawings. While the invention is described in conjunction with the embodiments below, it is understood that they are not intended to limit the invention to these embodiments and examples. On the contrary, the invention is intended to cover alternatives, modifications and equivalents, which can be included within the spirit and scope of the invention as defined by the appended claims. Furthermore, in the following detailed description of the present invention, numerous specific details are set forth in order to more fully illustrate the present invention. However, it is apparent to one of ordinary skill in the prior art having the benefit of this disclosure that the present invention can be practiced without these specific details. In other instances, well-known methods and procedures, components and processes have not been described in detail so as not to unnecessarily obscure aspects of the present invention. It is, of course, appreciated that in the development of any such actual implementation, numerous implementation-specific decisions must be made in order to achieve the developer's specific goals, such as compliance with application and business-related constraints, and that these specific goals vary from one implementation to another and from one developer to another. Moreover, it is appreciated that such a development effort can be complex and time-consuming but is nevertheless a routine undertaking of engineering for those of ordinary skill in the art having the benefit of this disclosure.

Homeostasis of the amino acid pool is critical to human physiology and influences the growth of commensals. The gut microbiota plays a profound role in maintaining the stable state of host nutrition through its de novo biosynthesis of amino acids. Since dietary lysine is limited, recent studies suggested that the gut-microbiota-derived amino acids are essential for maintaining systemic level of lysine.

Methylation of N-terminal amino groups is a ubiquitous reaction in all domains of life. Most studies mentioning lysine methylation are related to histone modification. In addition, lysine methylations are also observed in ribosomes, myosin and bacterial pili. Specifically, previous studies demonstrated that Nε-methyl-L-lysine is present in bacterial flagellar protein. Notably, free Nε-Methyl-L-lysine has been detected in human plasma, and the concentrations are higher in fasted subjects than nonfasted subjects.

DUSP6, a member of the MAPK phosphatase family, negatively regulates the target kinases by the dephosphorylation of serine/threonine and tyrosine residues. In mice, the expression of Dusp6 can increase fasting blood glucose by enhancing hepatic gluconeogenesis. A high-fat diet (HFD) has been shown to enhance Dusp6 expression in WAT (white adipose tissue). In a microbiome-dependent manner, Dusp6 deficiency has been shown to protect mice from diet-induced obesity by harboring a unique leanness-associated gut microbiome. Here it is shown that the downregulation of intestinal Dusp6 is critical for modulating the browning function of a cold- or fasting-adapted microbiome.

As shown in FIG. 1, during the cold-room temperature (CR) or fasting-refed (FR) transition, reduced Dusp6 expression changes mucin glycosylation to downregulate *Akkermansia muciniphila* and trigger the microbiota rearrangement for a Clostridia/Lachnospiraceae-dominant enterotype. When undergoing CR or FR transition, the pharmacological inhibition of DUSP6 can maintain the browning-associated composition and function of gut microbiota when control mice change their gut microbiota to the normal composition with no browning function.

Figure 2A:
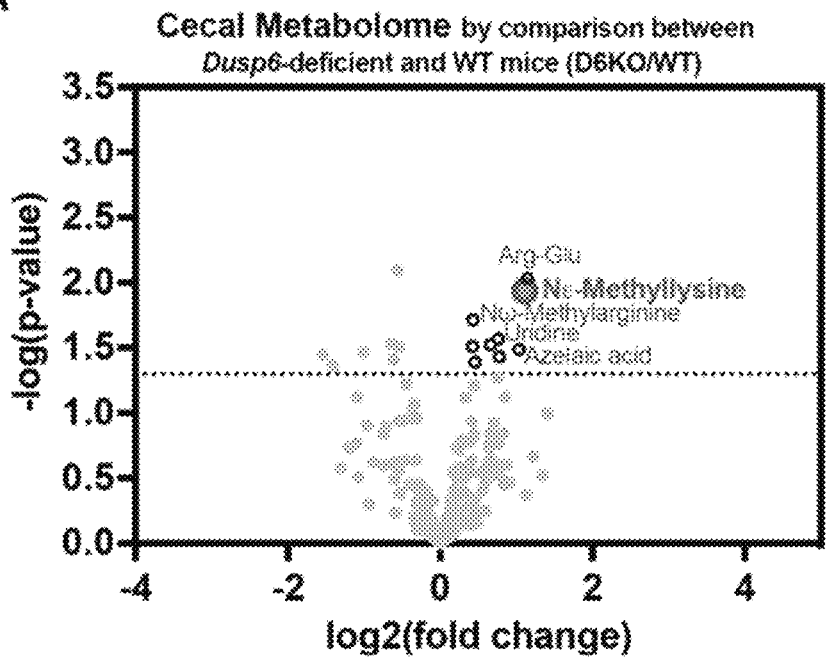
FIGS. 2A-2G illustrates some experimental results in accordance with some embodiments. (A) of FIG. 2A shows a volcano plot of CE-MS metabolome analyses on cecal contents collected from Dusp6-deficient (D6KO) or WT (wild type) mice. The metabolites upregulated by Dusp6 depletion are indicated by black circle or red circle. N=5 mice of each group. Cutoff of p value is <0.05. (B-C) of FIGS. 2B and 2C show Nε-Methyl-L-lysine quantification in the cultural supernatant (B) and pellets (C) of lysates extracted from *Akkermansia muciniphila, Bifidobacterium pseudolongum* and *Marvinbryantia formatexigens* through LC-MS/MS analysis. (D-E) of FIGS. 2D and 2E show Total tissue mass of pWAT (D) and iWAT (E) of FIG. 2E shows in chow diet-fed male mice orally administrated with Vehicle (H$_2$O), Nε-Methyl-L-lysine and L-lysine for fourteen days. N=6-8 mice of each group. (F) of FIG. 2F shows Representative images of H&E stained FFPE sections of pWAT and iWAT tissues of vehicle- or Nε-Methyl-L-lysine-treated mice. Scale bars, 50 μm. (G) of FIG. 2G shows Representative images of H&E-stained or Trichrome-stained FFPE sections of liver tissues collected from CD or CDAHFD fed mice with the vehicle, L-lysine, or Nε-Methyl-L-lysine administration. Scale bar, 50 μm. Data are presented as mean±SEM. ns, statistically non-significant; *P<0.05; P<0.01; *P<0.001 according to One-Way ANOVA analysis and Tukey post-hoc test. No collected data were excluded for analysis.

As shown in FIG. 2A, by performing untargeted CE-MS metabolome analyses on cecal contents of WT littermates and Dusp6-deficient mice, we identified Nε-Methyl-L-lysine that is upregulated by Dusp6-deficiency.

Figure 1B:
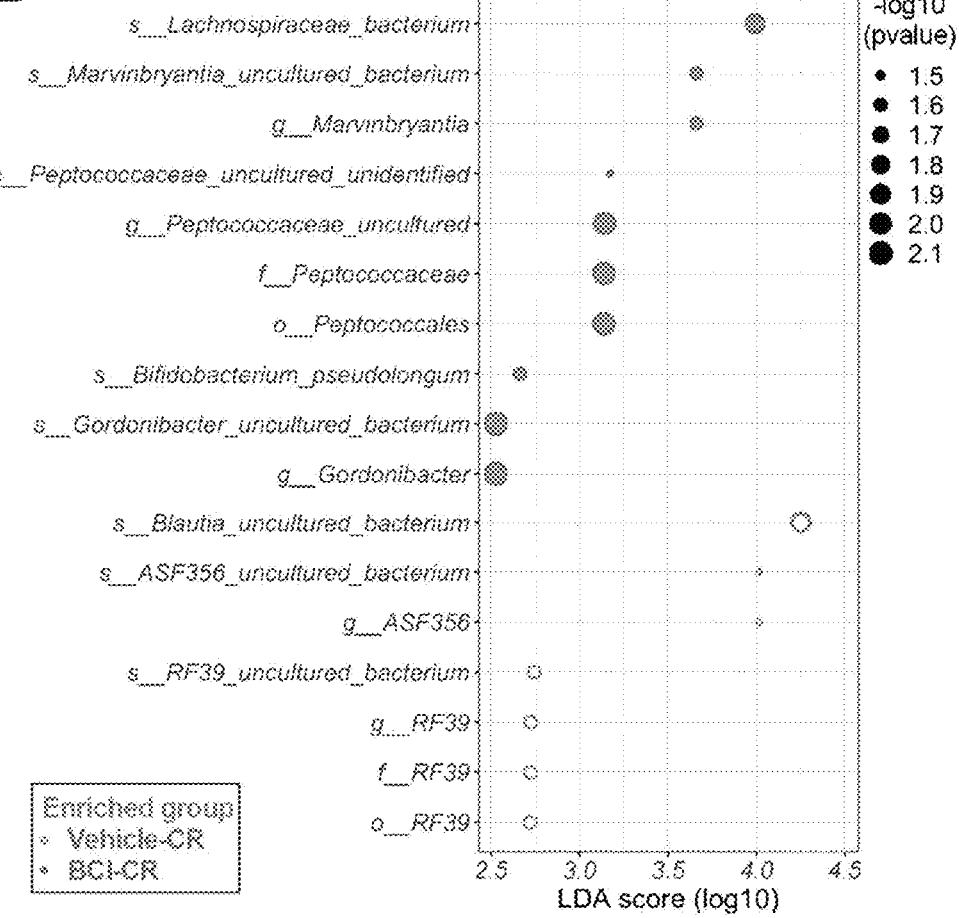
FIG. 1B illustrates the cold induced gut bacteria that is regulated by DUSP6 inhibition by injecting DUSP6 inhibitor, (E/Z)-BCI hydrochloride, into the mice underwent cold-room temperature (CR) transition.

To search the potential Nε-Methyl-L-lysine producers in cold microbiota, we performed the microbiota analysis on 16S rRNA sequencing data of BCI-CR and Vehicle-CR microbiota. We found that during the cold-RT transition, the DUSP6 inhibition significantly regulates the abundance of Lachospiraceae bacterium, *Marvinbryantia* uncultured bacterium, Peptococcaceae uncultured bacterium, *Bifidobacterium pseudolongum* and Gordonnibacter uncultured bacterium (FIG. 1B).

It further identified Nε-Methyl-L-lysine, produced by *Marvinbryantia formatexigens*, as an adipose-regulating metabolite with potential for treating fatty liver and nonalcoholic hepatic steatosis (NASH) in mice. In this disclosure, it is identified the Dusp6-*A. muciniphila* axis as a molecular switch inducing a browning microbiota that influences the rapid adaptation of host metabolism to environmental challenges.

To confirm the relationship between Nε-Methyl-L-lysine and the WAT, following tests and analyses are performed.

Experimental Animals, Experiment Design and Result

To test the browning-activating and WAT-reducing abilities of Nε-Methyl-L-lysine, 8-week-old male C57BL/6J mice were orally administrated of L-lysine (150 mM), Nε-Methyl-L-lysine (150 mM) (100 ul/mouse/Day) or vehicle (water; 100 ul/mouse/Day) for 14 days.

Adipose Tissues Reducing Experiment 14 days after treatment, the L-lysine (150 mM), Nε-Methyl-L-lysine (150 mM) (100 ul/mouse/Day) or vehicle (water; 100 ul/mouse/Day) treated mice were sacrificed and the perigonadal white adipose tissue (pWAT) and inguinal white adipose tissue (iWAT) were collected and weighted for measuring the reducing effects of L-lysine, Nε-Methyl-L-lysine and vehicle. To test the browning-activating abilities of L-lysine, Nε-Methyl-L-lysine and vehicle control in pWAT and iWAT of treated mice, total RNA of WAT was extracted by using RNeasy Lipid Tissue kits. The concentration and quality of RNA were measured by NanoDrop spectrophotometer. For qRT-PCR analysis of browning marker gene Ucp1 and beta-oxidation gene Cpt1b, complementary DNA was obtained by using M-MLV Reverse Transcriptase with oligo-dT primers. qRT-PCR was performed with SYBR-green master on a MyGo Pro PCR system.

Gut Microbiota Control Experiment 14 days after treatment, the fecal pellets of L-lysine (150 mM), Nε-Methyl-L-lysine (150 mM) (100 ul/mouse/Day) or vehicle (water; 100 ul/mouse/Day) treated mice were collected for DNA extraction. PCR amplification was performed on extracted DNA for 16s rDNA amplicons by using the primers targeting the V3-V4 region (primer set: 341F-805R). 16s rRNA amplicons were sequenced on an Illumina Miseq platform and generated 300 bp paired-end reads. Raw data were obtained with barcodes sequences cleaned up. The sequencing data was analyzed using the QIIME 2 platform (version: 2020.8).

Metabolome Analyses 30-50 mg cecal contents of each mouse was resuspend in extraction buffer containing internal standards and centrifuged. The supernatant of samples was transferred into a prewashed ultrafiltration column (5 kDa cutoff, UltrafreeMC-PLHCC) and centrifuged at 9,100×g for 1 hours at 4° C. Cecal metabolome was profiled by using Capillary Electrophoresis Time-of-Flight Mass Spectrometry (CE-TOFMS) in two modes for cationic and anionic metabolites.

LC-MS/MS Analyses

For targeted detection of Nε-Methyl-L-lysine, the cultural supernatant and pellets of *Bifidobacterium pseudolongum, Akkermansia muciniphila* and *Marvinbryantia formatexigens* were collected and lyophilized by freeze dryer. The resultant dry residues were reconstituted in 500 μL of Acetonitrile/Water (1:1) and subjected to the LC-MS/MS analysis.

Histological Examination

Tissues were fixed in 4% neutral-buffered formalin (Sigma), paraffin-embedded, sectioned, and stained with hematoxylin and eosin (H&E) or subjected to immunohistochemistry analysis. For adipose tissue, the 5 μm FFPE sections of pWAT and iWAT were deparaffinated and stained with H&E. The mean adipocyte area and adipocyte size distribution were determined by using Adiposoft software. For quantifying lipid droplets in liver tissues, the 5 μm FFPE liver sections were deparaffinated and stained with H&E. The mean lipid droplets area was determined by using Image J software.

NASH and Liver Fibrosis Test

Groups of 6-week-old male C57BL/6J mice were fed in choline-deficient, L-amino acid-defined, high-fat diet (CDAHFD; #A06071302) purchased from Research Diets (New Brunswick, NJ, USA) or chow diet for 4 weeks. After two weeks of CDAHFD treatment, mice were orally administrated L-lysine (150 mM), Nε-Methyl-L-lysine (150 mM) (100 ul/mouse/Day) or vehicle (water; 100 ul/mouse/Day) for 14 days with continuing CDAHFD treatment. Body-weight was measured weekly. After sacrifice, the serum of mice was collected and stored at −80° ° C. The serum levels of aspartate aminotransferase (AST) and alanine aminotransferase (ALT) were measured with biochemistry slides for a chemistry analyzer (FUJI DRI-CHEM 4000i, Fujifilm Corporation, Japan). For hepatic fibrosis staining, the 5 μm FFPE liver sections were deparaffinated and stained with a Trichrome staining kit according to the manufacturer's instructions.

Cell Differentiation Experiment

The differentiation of 3T3-L1 cells was performed by using 3T3-L1 DIFFERENTIATION KIT (DIF001, Merck). After differentiation, cells were maintained in a complete medium containing 50 μM Nε-Methyl-L-lysine and vehicle control for 7 days before the harvest. After treatments, cells were subjected to RNA extraction and qPCR analysis of Ucp1 and Cpt1b mRNA expression. For quantifying the lipid accumulation in cells, cells were fixed with in 4% neutral-buffered formalin and stained with Oil Red-O reagent.

By performing metabolome analyses on cecal contents of WT littermates and Dusp6-deficient mice, it is identified a unique cecal metabolite, Nε-Methyl-L-lysine, which has been found in the plasma of fasting humans (FIG. 2A). It is therefore verified that Nε-Methyl-L-lysine is able to be produced by Dusp6-*A. muciniphila*-axis-regulated bacteria.

Figure 2B:
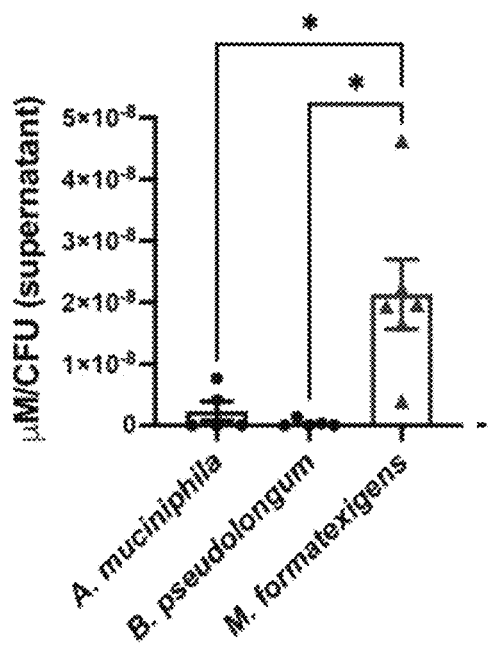
Figure 2C:
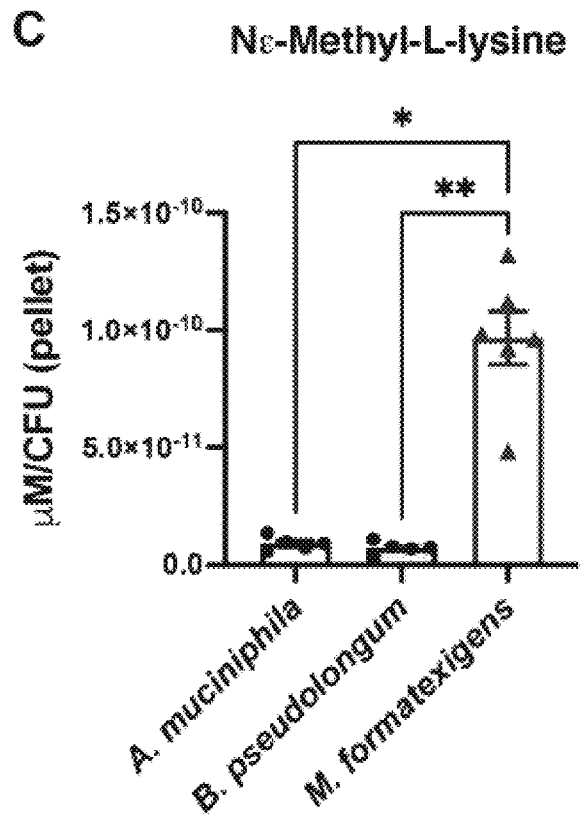
Figure 3A:
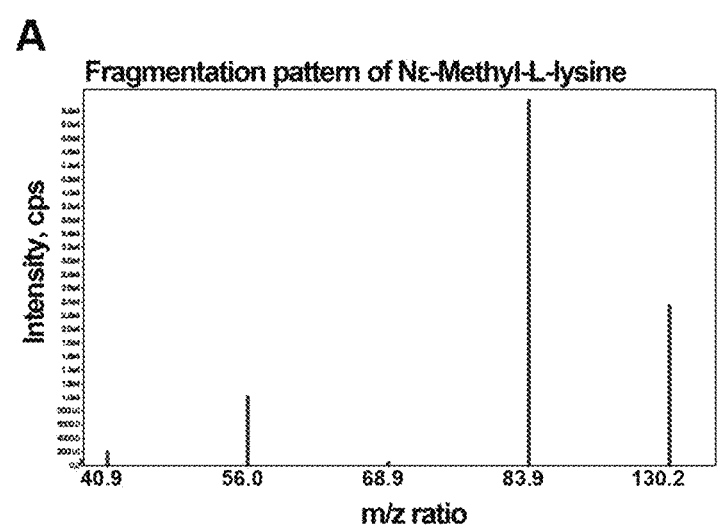

By LC-MS/MS analyses (FIG. 3A), it is detected significantly higher levels of Nε-Methyl-L-lysine in both the supernatant and pellet of *Marvinbryantia formatexigens* (Lachnospiraceae) extracts whereas *A. muciniphila* and *Bifidobacterium pseudologum* expressed Nε-Methyl-L-lysine at a very low level (FIGS. 2B and 2C). This result suggests that Dusp6-*A. muciniphila*-Lachnospiraceae axis may regulate host physiology by modulating the expression level of specific metabolites, such as Nε-Methyl-L-lysine.

Figure 3B:
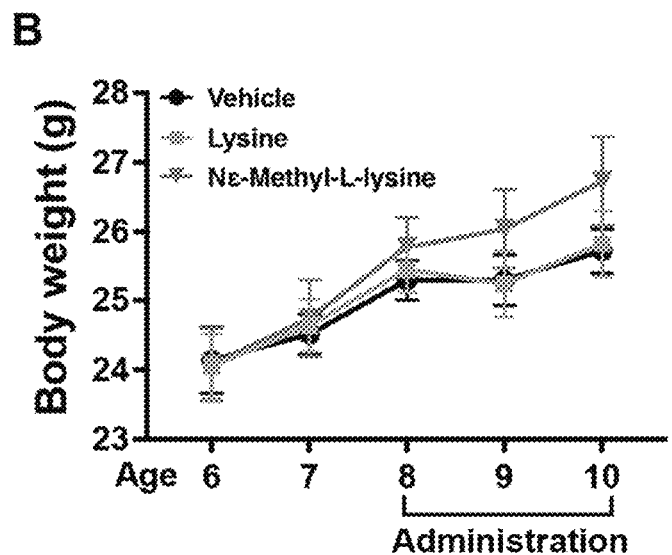
Figure 3C:
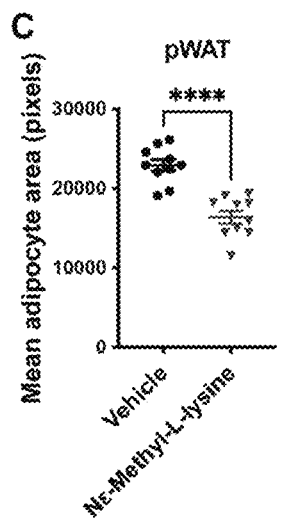
Figure 3D:
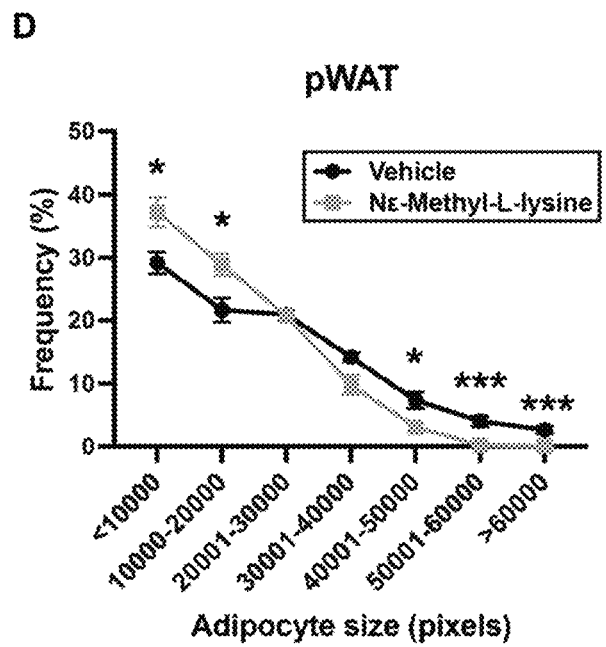
Figure 3E:
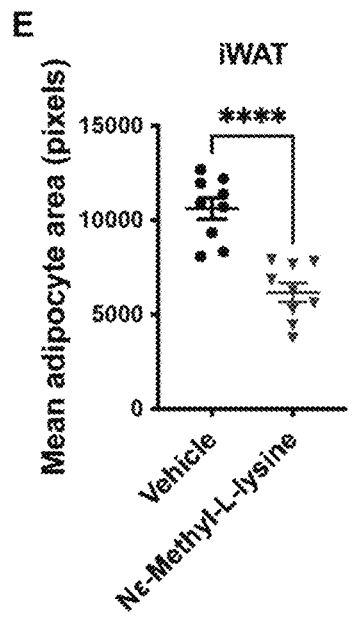
Figure 3F:
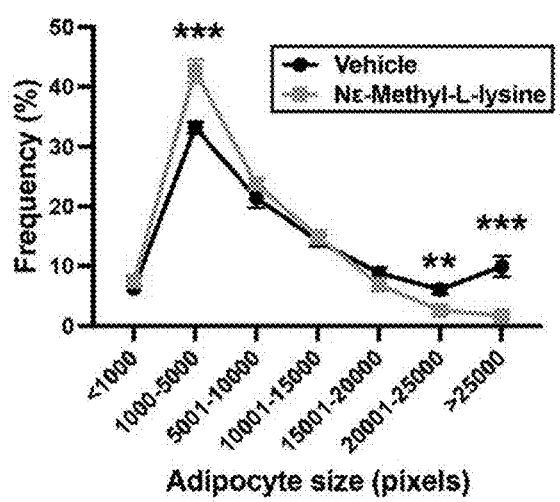

Intestinal microbial lysine has been shown to significantly contribute to the whole-body lysine homeostasis in humans. However, whether specific bacterial modification of lysine can impact host physiology is unknown. In chow-diet-fed mice, oral administration of Nε-Methyl-L-lysine for fourteen days did not significantly change the body weight of treated mice (FIG. 3B). This finding indicates that Nε-Methyl-L-lysine did not interfere with energy absorption in mice.

Surprisingly, Nε-Methyl-1-lysine dramatically reduced the total mass of pWAT and iWAT (FIGS. 2D and 2E), and also enhanced the expression of Ucp-1 and Cpt1b in pWAT (FIGS. 7a and 7b).

Figure 2D:
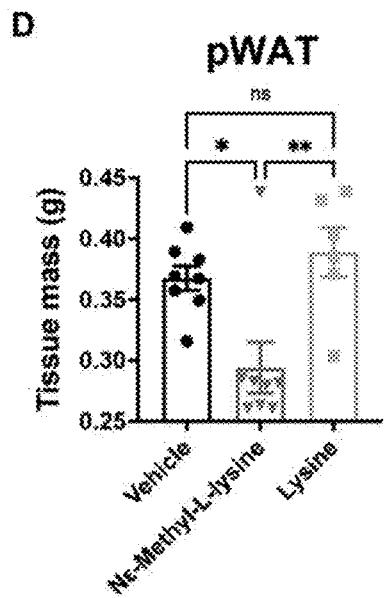
Figure 2E:
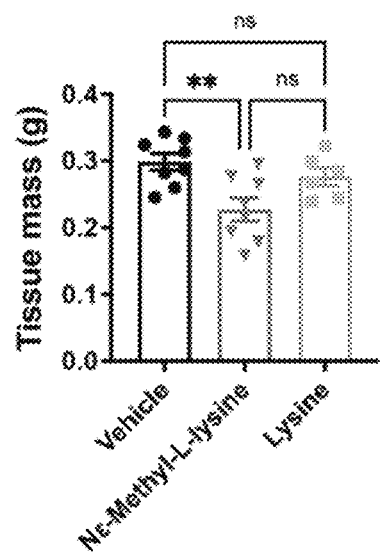
Figure 2F:
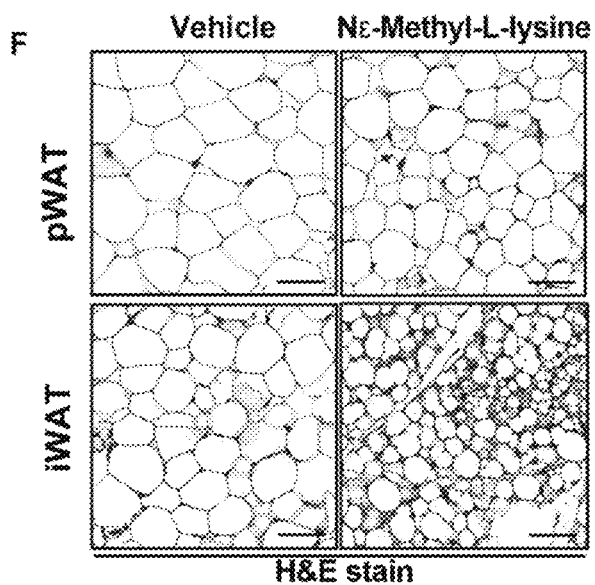

By histological examination, it is found that the administration of Nε-Methyl-L-lysine significantly reduced adipocyte size in both pWAT and iWAT (FIG. 2F). These results are confirmed by Adiposoft software, which shows that the mean adipocyte area and distribution of adipocyte size of pWAT and iWAT are significantly reduced in Nε-Methyl-L-lysine treated mice (FIG. 3C to 3F). The findings demonstrate that Nε-Methyl-L-lysine is a functional-microbiome-derived signaling molecule monitored by WAT.

Figure 2G:
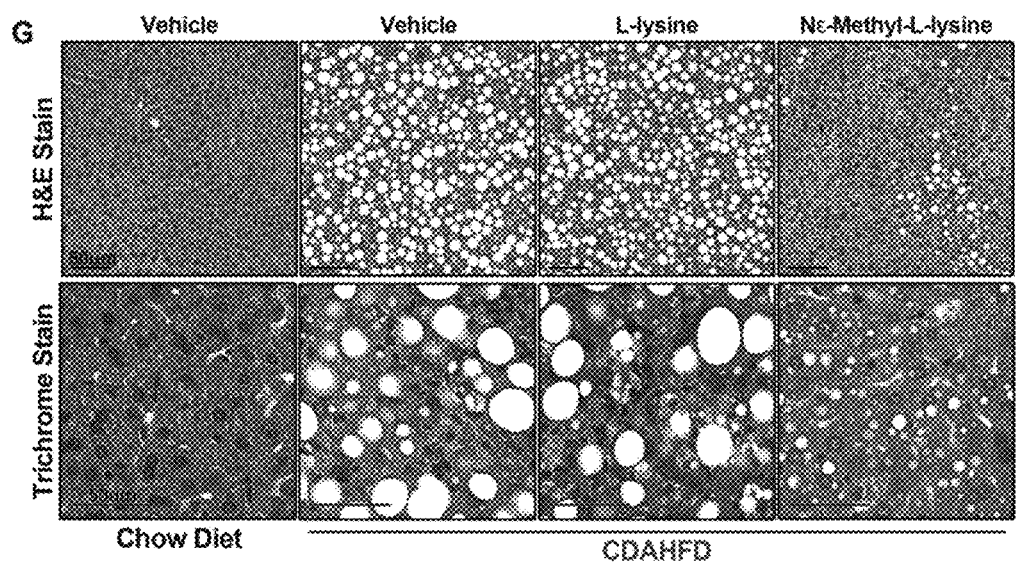
Figure 3G:
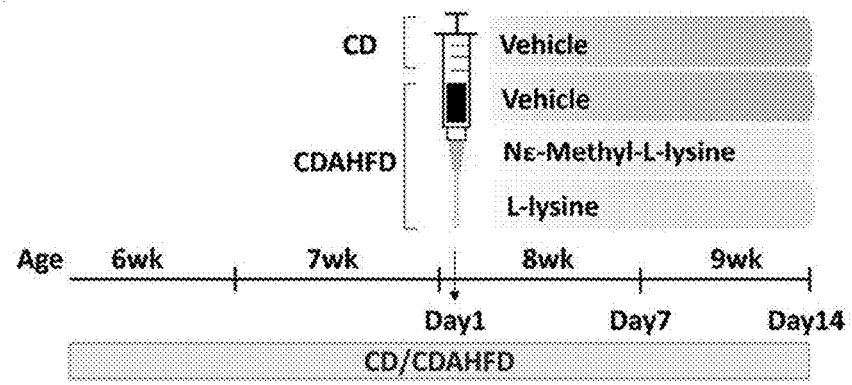
Figure 3H:
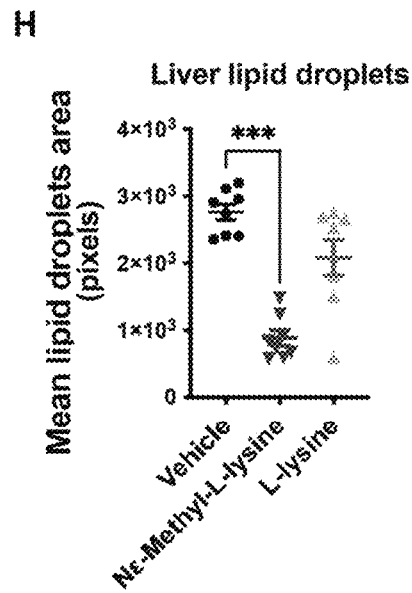
Figure 3I:
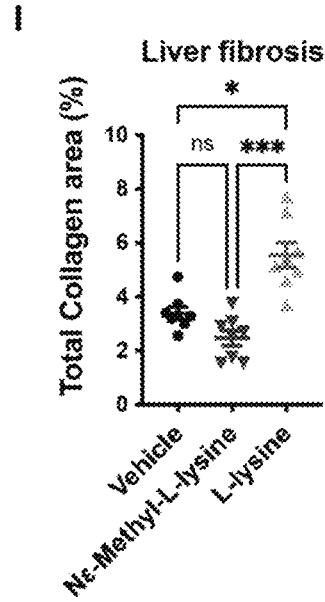
Figure 3J:
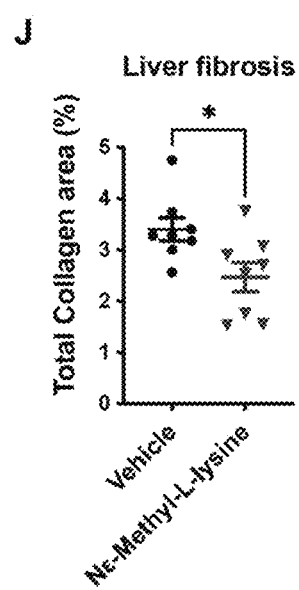

It is noticed that visceral pWAT has a higher sensitivity to Nε-Methyl-L-lysine than subcutaneous iWAT (FIGS. 2D and 2E). To understand the effects of Nε-Methyl-L-lysine on treating visceral-fat-associated diseases, a choline-deficient, L-amino acid-defined, high-fat diet (CDAHFD) is used to induce nonalcoholic steatohepatitis (NASH) in mice (FIG. 3G). Nε-Methyl-L-lysine shows a promising effect on reducing the liver lipid droplets (FIG. 2G and FIG. 3H), and fibrosis (FIG. 2G, FIGS. 3I and 3J) in mice fed with a CDAHFD.

Figure 4:
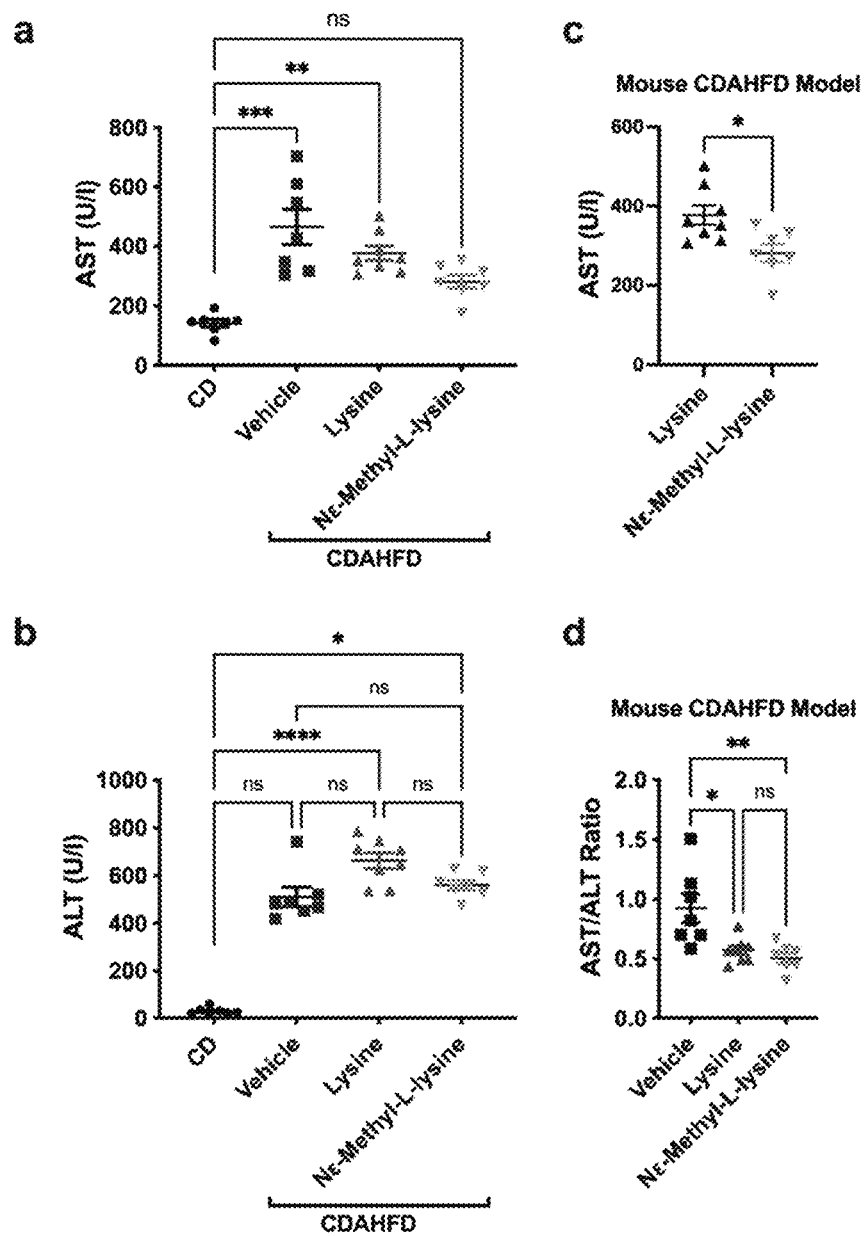
FIG. 4 illustrates ALT, AST, and AST/ALT ratio data of tests (a-d) in accordance with some embodiments.

FIG. 4 shows the effects of Nε-Methyl-L-lysine on treating NASH and liver fibrosis. 8-weeks old male C57BL/6 mice are fed with a choline-deficient, L-amino acid-define, high-fat diet (CDAHFD) (Research Diet, Inc. A060671302) for 4 weeks to induce NASH and liver fibrosis. During the third and fourth week of CDAHFD treatment, it is orally administered Nε-Methyl-L-lysine (100 μg Nε-Methyl-L-lysine/g body weight/per day) into mice for fourteen days. When compared with chow-diet fed mice, CDAHFD significantly increased the serum AST level in vehicle- and lysine-treated group but not in Nε-Methyl-L-lysine-treated group. When compared with chow-diet fed mice, CDAHFD significantly increased the serum ALT (alanine transaminase) level in lysine- and Nε-Methyl-L-lysine-treated group but not in vehicle-treated group. Nε-Methyl-L-lysine showed a better effect than lysine on reducing serum AST level and AST/ALT ratio in mice fed with a CDAHFD. Data are presented as mean±SEM. Kruskal-Wallis test is used in FIG. 4 (a and b) Mann-Whitney t-tests are used in FIG. 4 (c and d) to indicate significant differences between groups. *P<0.05. *P<0.005. *P<0.0005. *P<0.00005.

In some embodiments, Nε-Methyl-L-lysine has a predetermined dose in a range of 0.0001-100 mg/g body weight to reduce AST level or ALT level or AST/ALT ratio in subjects diagnosed in need of treatment for nonalcoholic fatty liver disease, nonalcoholic steatohepatitis (NASH), liver fibrosis and liver cirrhosis or hepatoma. In some embodiments, the above mentioned Nε-Methyl-L-lysine predetermined dose is in a range of 0.0001-0.0010 mg/g body weight. In some other embodiments, the above mentioned Nε-Methyl-L-lysine predetermined dose is in a range of 0.0011-0.0100 mg/g body weight. In some other embodiments, the above mentioned Nε-Methyl-L-lysine predetermined dose is in a range of 0.0110-0.100 mg/g body weight. In some other embodiments, the above mentioned Nε-Methyl-L-lysine predetermined dose is in a range of 0.1-1.000 mg/g body weight. In some other embodiments, the above mentioned Nε-Methyl-L-lysine predetermined dose is in a range of 1.1-10 mg/g body weight. In some other embodiments, the above mentioned Nε-Methyl-L-lysine predetermined dose is in a range of 10-100 mg/g body weight.

These results provide that Nε-Methyl-L-lysine can alleviate the liver damage caused by excessive lipid storage. Detailed molecular analysis shows how Nε-Methyl-L-lysine reduces adiposity and hepatic lipid accumulation. Altogether, it is identified the Dusp6-Akkermansiaceae axis as a critical host control mechanism regulating mucosal-to-luminal microbiota rearrangements. The Dusp6-Akkermansiaceae-Lachnospiraceae axis contributes to the remodeling of cold- and fasting-adapted microbiomes to activate browning signaling in WAT via specific metabolites.

Figure 5:
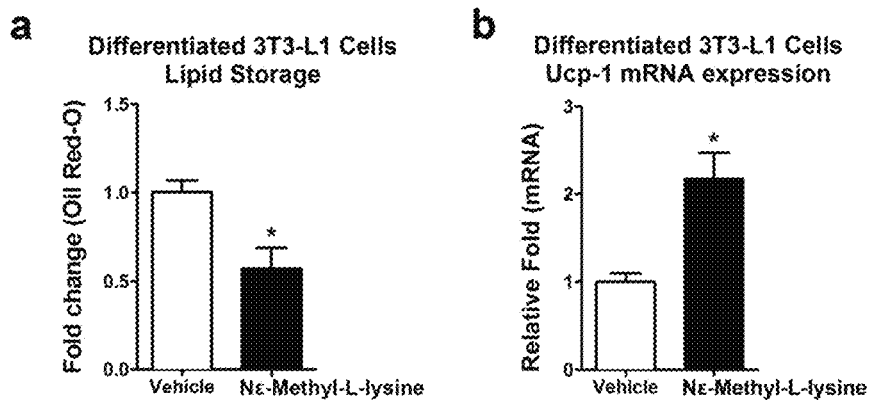
FIG. 5 illustrates a method of using Nε-Methyl-L-lysine to inhibit lipid storage and promote adipose browning in differentiated 3T3-L1 adipocytes in accordance with some embodiments.

FIG. 5 illustrates a method of using Nε-Methyl-L-lysine to inhibit lipid storage and promote adipose browning in differentiated 3T3-L1 adipocytes in accordance with some embodiments. 3T3-L1 cells (SP-L1-F) are purchased from a commercial available source. It is maintained and differentiated 3T3-L1 preadipocytes. After differentiation, differentiated 3T3-L1 adipocytes are treated by post-differentiation medium containing vehicle ($H_2O$) or Nε-Methyl-L-lysine (150 μM). When quantified lipid content of vehicle-treated and Nε-Methyl-L-lysine-treated cells by using oil-red O staining, it is found that Nε-Methyl-L-lysine can significantly reduce lipid storage of differentiated 3T3-L1 adipocytes (FIG. 5a). We further confirmed that Nε-Methyl-L-lysine could significantly induce browning marker Ucp-1 expression in 3T3-L1 adipocytes than vehicle-treated cells (FIG. 5b). These results provide that Nε-Methyl-L-lysine is an important modulator for regulating adipose functions. Data are collected from three independent experiments (FIGS. 5a and 5b) and presented as mean±SEM. Mann-Whitney t-tests are used to indicate significant differences between groups. *$P<0.05$. $P<0.01$. **$P<0.0001$.

Figure 6:
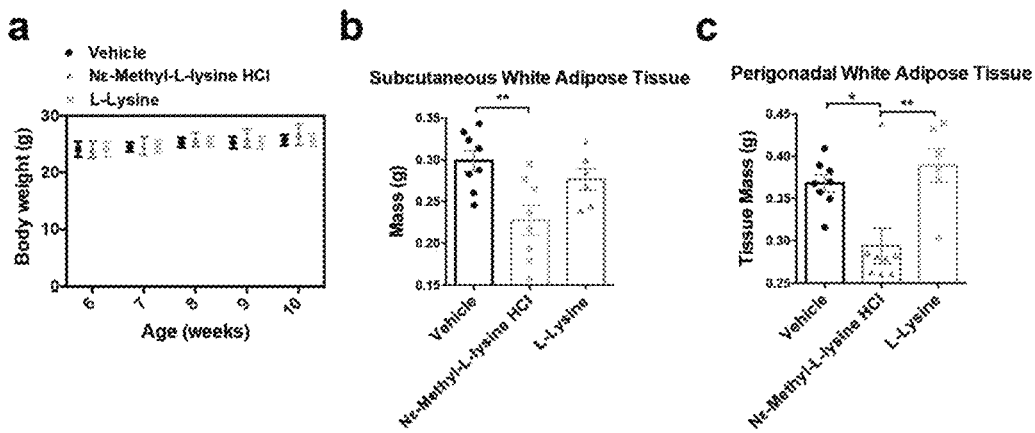
FIG. 6 illustrates a method of using Nε-Methyl-L-lysine to reduce the total mass of subcutaneous and perigonadal white adipose tissues without reducing total body weight in accordance with some embodiments.

FIG. 6 illustrates a method of using Nε-Methyl-L-lysine to reduce the total mass of subcutaneous and perigonadal white adipose tissues without reducing total body weight. It is orally administered Nε-Methyl-L-lysine (100 μg Nε-Methyl-L-lysine/g body weight/per day, body weights before treatment, body weights 7 days after treatment, body weights 14 days after treatment) into eight weeks old male C57/BL6 mice for fourteen days. It is found that Nε-Methyl-L-lysine did not change the mice body weights when compared with the mice treated with vehicle ($H_2O$, body weights before treatment, body weights 7 days after treatment, body weights 14 days after treatment) or an equal amount of L-lysine (100 μg L-lysine/g body weight/per day, body weights before treatment, body weights 7 days after treatment, body weights 14 days after treatment) (FIG. 6a). This method dramatically reduced the total mass of subcutaneous white adipose tissues (FIG. 6b) and perigonadal white adipose tissues (FIG. 6c) in treated mice. In contrast, the vehicle and L-lysine did not show significant effects (FIGS. 6b and 5c). Data are presented as mean±SEM and significance is calculated by one-way ANOVA followed by Tukey's multiple comparison test. *$P<0.05$. **$P<0.01$.

Figure 7:
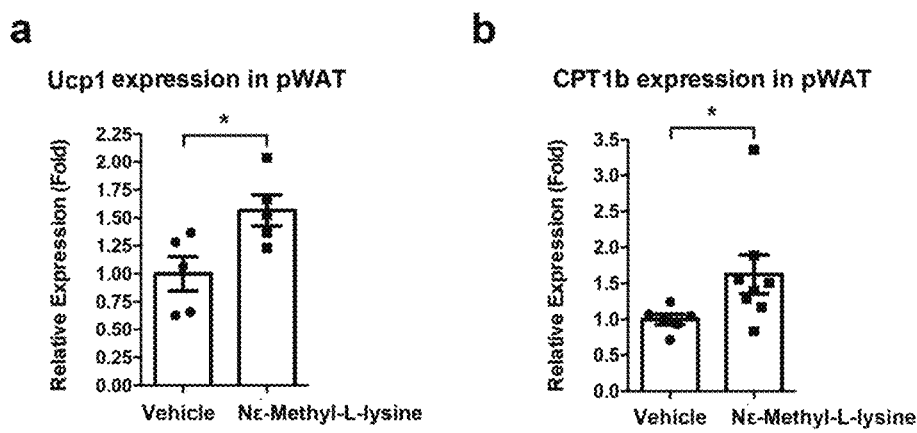
FIG. 7 illustrates a method of using Nε-Methyl-L-lysine to promote adipose beiging and β-oxidation in white adipose tissues in accordance with some embodiments.

Beiging and β-oxidation are two major fat-burning mechanism of white adipose tissues controlled by the expression of Ucp-1 and CPT-1 gene respectively. FIG. 7 shows the mechanism of Nε-Methyl-L-lysine in reducing adiposity. It is orally administered Nε-Methyl-L-lysine (100 μg Nε-Methyl-L-lysine/g body weight/per day) into eight weeks old male C57/BL6 mice for fourteen days. 14 days after treatment, perigonadal adipose tissues of vehicle ($H_2O$) treated mice and Nε-Methyl-L-lysine treated mice are collected for qPCR analyses. Nε-Methyl-L-lysine significantly induced the expression of Ucp-1 (browning marker gene) and CPT-1b (β-oxidation marker gene) genes in white adipose tissues to activate the adipose browning and β-oxidation respectively in the white adipose tissues (FIGS. 7a and 7b). Data are presented as mean±SEM. Mann-Whitney t-tests are used to indicate significant differences between groups. *$P<0.05$.

In some embodiments, Nε-Methyl-L-lysine is a predetermined metabolite used as a leanness-associated or anti-obese substance. In some embodiments, Nε-Methyl-L-lysine is a predetermined metabolite used to reduce the percentage of white adipose tissues of total body weight. In some embodiments, Nε-Methyl-L-lysine is a predetermined metabolite used to converting white adipose cells to beige adipose cells. In some embodiments, Nε-Methyl-L-lysine is a predetermined metabolite used to reduce the number of white adipocytes in white adipose tissues. In some embodiments, Nε-Methyl-L-lysine is a predetermined metabolite used to increase the number of beige adipocytes in white adipose tissues.

In some embodiments, Nε-Methyl-L-lysine having a predetermined dose in a range of 0.0001-100 mg/g body weight to reduce the percentage (1% to 10%) of white adipose tissues of total body weight, to converting white adipose cells to beige adipose cells, to reduce the number of white adipocytes in white adipose tissues, to increase the number of beige adipocytes in white adipose tissues. In some embodiments, the above mentioned Nε-Methyl-L-lysine predetermined dose is in a range of 0.0001-0.0010 mg/g body weight. In some other embodiments, the above mentioned Nε-Methyl-L-lysine predetermined dose is in a range of 0.0011-0.0100 mg/g body weight. In some other embodiments, the above mentioned Nε-Methyl-L-lysine predetermined dose is in a range of 0.0110-0.100 mg/g body weight. In some other embodiments, the above mentioned Nε-Methyl-L-lysine predetermined dose is in a range of 0.1-1.000 mg/g body weight. In some other embodiments, the above mentioned Nε-Methyl-L-lysine predetermined dose is in a range of 1.1-10 mg/g body weight. In some other embodiments, the above mentioned Nε-Methyl-L-lysine predetermined dose is in a range of 10-100 mg/g body weight.

Figure 9:
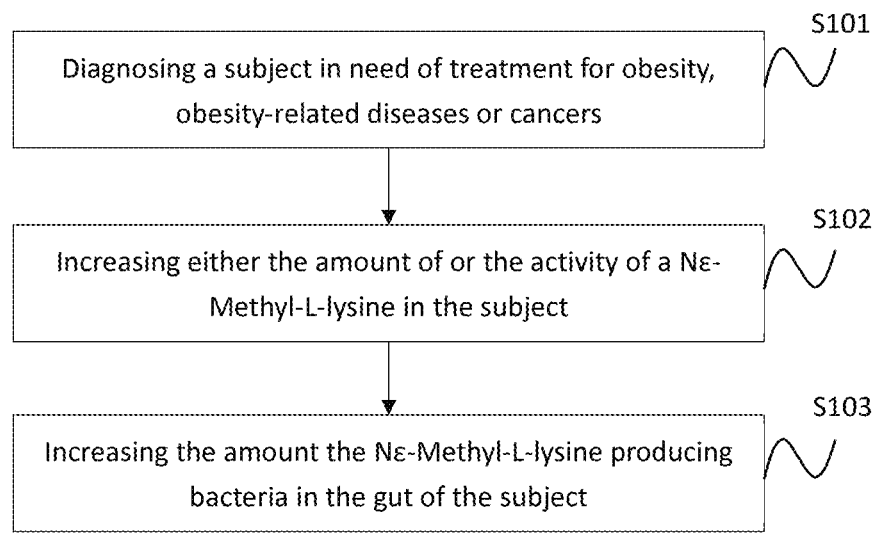
FIG. 9 illustrates a flow chart of the method for treating obesity, obesity-related diseases or solid tumors.

FIG. 9 illustrates a flow chart of the method for treating obesity, obesity-related diseases, or solid tumors. The method comprises: S101, diagnosing a subject in need of treatment for obesity, obesity-related diseases or, cancers; S102, increasing either the amount of or the activity of a Nε-Methyl-L-lysine in the subject; and S103, increasing the amount the Nε-Methyl-L-lysine producing bacteria in the gut of the subject.

In some embodiments, diagnosing a subject in need of treatment for obesity, obesity-related diseases, metabolic syndrome, type II diabetes, hypertension, cardiovascular disease, nonalcoholic fatty liver disease, nonalcoholic steatohepatitis (NASH), liver fibrosis and liver cirrhosis or cancers, oral administration or intravenous (IV) injection or intramuscular (IM) injection of Nε-Methyl-L-lysine or Nε-Methyl-L-lysine hydrochloride, or oral administration of Nε-Methyl-L-lysine producing bacteria are used to increase the amount of Nε-Methyl-L-lysine in a subject as a treatment. In some embodiments, diagnosing a subject with cancers in need of chemotherapy or immunotherapy, oral administration or intravenous (IV) injection or intramuscular (IM) injection of Nε-Methyl-L-lysine or Nε-Methyl-L-lysine hydrochloride, or oral administration of Nε-Methyl-L-lysine producing bacteria are used to increase the amount of Nε-Methyl-L-lysine in a subject as a treatment.

In some embodiments, increasing the activity of a Nε-Methyl-L-lysine in the subject in need of treatment for obesity, obesity-related diseases, metabolic syndrome, type II diabetes, hypertension, cardiovascular disease, nonalcoholic fatty liver disease, nonalcoholic steatohepatitis, liver fibrosis and liver cirrhosis or cancers.

In some embodiments, the amount of or the activity of the Nε-Methyl-L-lysine is increased by administration of a DUSP6 antagonist to the subject in need of treatment for obesity, obesity-related diseases, metabolic syndrome, type II diabetes, hypertension, cardiovascular disease, nonalcoholic fatty liver disease, nonalcoholic steatohepatitis, liver fibrosis and liver cirrhosis or cancers.

In some embodiments, Nε-Methyl-L-lysine having a predetermined dose in a range of 0.0001-100 mg/g body weight are used to treat the subject in need of treatment for obesity, obesity-related diseases, metabolic syndrome, type II diabetes, hypertension, cardiovascular disease, nonalcoholic fatty liver disease, nonalcoholic steatohepatitis, liver fibrosis and liver cirrhosis or cancers. In some embodiments, the above mentioned Nε-Methyl-L-lysine predetermined dose is in a range of 0.0001-0.0010 mg/g body weight. In some other embodiments, the above mentioned Nε-Methyl-L-lysine predetermined dose is in a range of 0.0011-0.0100 mg/g body weight. In some other embodiments, the above mentioned Nε-Methyl-L-lysine predetermined dose is in a range of 0.0110-0.100 mg/g body weight. In some other embodiments, the above mentioned Nε-Methyl-L-lysine predetermined dose is in a range of 0.1-1.000 mg/g body weight. In some other embodiments, the above mentioned Nε-Methyl-L-lysine predetermined dose is in a range of 1.1-10 mg/g body weight. In some other embodiments, the above mentioned Nε-Methyl-L-lysine predetermined dose is in a range of 10-100 mg/g body weight.

In some embodiments, wherein the subject described above is selected from the group consisting of a human, a dog, a cat, a cow, a horse, a rabbit, a pig, a goat, an avian species and a fish species.

Above mentioned treatments can be applied by comparing the physiological data (e.g., bogy fat or a fat content in a predetermined organ) before, during, and/or after a predetermined treatment or treatment data from collected treatment data of others or prior treatment data of the same person, and adjust the dosage or amount of application accordingly.

Figure 8:
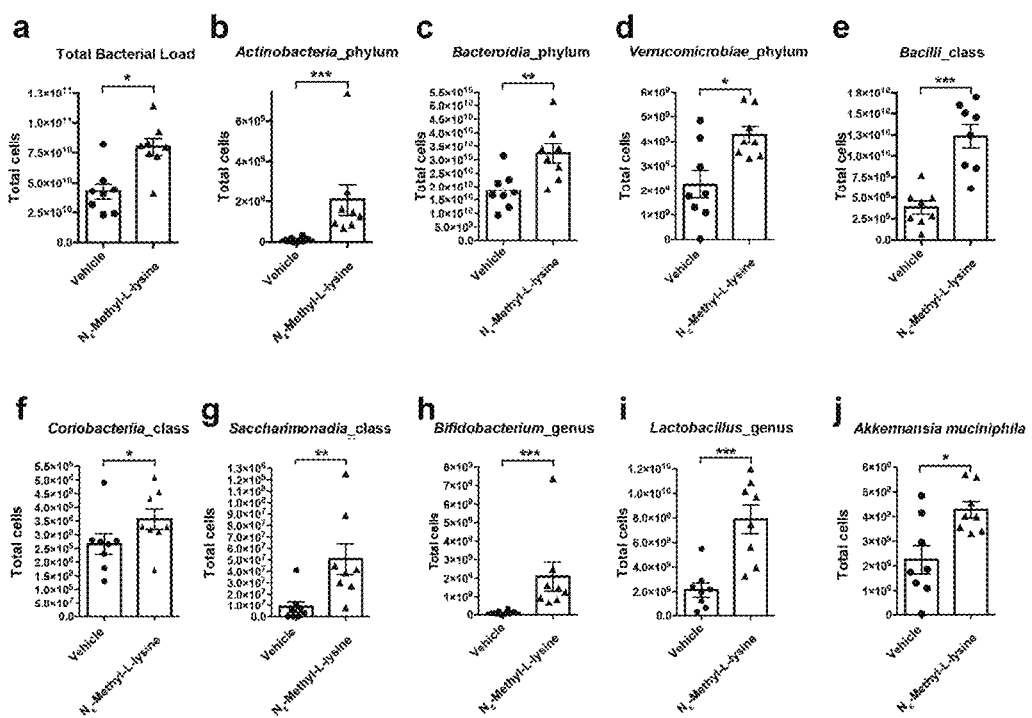
FIG. 8 illustrates a method of using Nε-Methyl-L-lysine to increase the abundance of beneficial gut bacteria in the gut in accordance with some embodiments.

FIG. 8 shows the effects of Nε-Methyl-L-lysine on modulating gut microbiota. It is orally administered Nε-Methyl-L-lysine (100 μg Nε-Methyl-L-lysine/g body weight/per day) into eight weeks old male C57/BL6 mice for fourteen days. Fourteen days after treatment, perigonadal adipose tissues of vehicle ($H_2O$) treated mice and Nε-Methyl-L-lysine treated mice were collected for qPCR analyses. Nε-Methyl-L-lysine is capable of increasing the total bacterial load (FIG. 8a) that is the important signature of a healthy gut microbiota. Nε-Methyl-L-lysine is capable of increasing the number of beneficial bacteria classified in the Actinobacteria phylum (FIG. 8b), Bacteroidia phylum (FIG. 8c), Verrucomicrobiota phylum (FIG. 8d), Bacilli class, Coriobacteriia class (FIG. 8f), Saccharimonadia class (FIG. 8g), *Bifidobacterium* genus (FIG. 8h), and *Lactobacillus* genus (FIG. 8i) in gut. Data are presented as mean±SEM. Mann-Whitney t-tests are used to indicate significant differences between groups. *P<0.05.

In some embodiments, Nε-Methyl-L-lysine is used to increase the number or relative percentage of beneficial gut bacteria *Akkernmansia muciniphilla* in gut (FIG. 8j).

In some embodiments, diagnosing a subject in need of treatment for altering the microbial composition of gut microbiota, oral administration or intravenous (IV) injection or intramuscular (IM) injection of Nε-Methyl-L-lysine or Nε-Methyl-L-lysine hydrochloride, or oral administration of Nε-Methyl-L-lysine producing bacteria are used to increase the amount of Nε-Methyl-L-lysine in a subject as a treatment.

In some embodiments, diagnosing a subject in need of treatment for increasing the number of total gut bacteria or the bacteria classified in the Actinobacteria phylum, Bacteroidia phylum, Verrucomicrobiota phylum, Bacilli class Coriobacteriia class, Saccharimonadia class, *Bifidobacterium* genus, and *Lactobacillus* genus, oral administration or intravenous (IV) injection or intramuscular (IM) injection of Nε-Methyl-L-lysine or Nε-Methyl-L-lysine hydrochloride, or oral administration of Nε-Methyl-L-lysine producing bacteria are used to increase the amount of Nε-Methyl-L-lysine in a subject as a treatment. Preferably, the amount of the Nε-Methyl-L-lysine producing bacteria in the gut of the subject is at least $10^5$ CFU and more preferably at least $10^8$ CFU.

Figure 10:
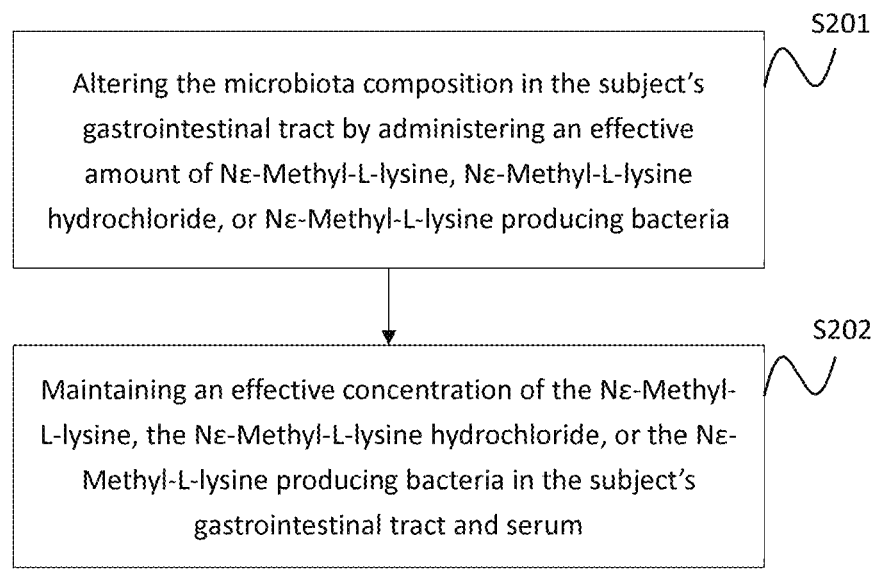
FIG. 10 illustrates a flow chart of the method for reducing a fat percentage in an organ.

FIG. 10 illustrates a flow chart of the method for reducing a fat percentage in an organ. The method comprises: S201, altering the microbiota composition in the subject's gastrointestinal tract by administering an effective amount of Nε-Methyl-L-lysine, Nε-Methyl-L-lysine hydrochloride, or Nε-Methyl-L-lysine producing bacteria; and S202, maintaining an effective concentration of the Nε-Methyl-L-lysine, the Nε-Methyl-L-lysine hydrochloride, or the Nε-Methyl-L-lysine producing bacteria in the subject's gastrointestinal tract and serum to reduce the BMI and body fat percentage. As the result, the BMI and body fat of the subject may be reduced due to the reduce 1% to 20% of total body fat or organ fat, preferably 10% to 20%.

In an embodiment, the effective amount administered is at least $10^5$ CFU and more preferably at least $10^8$ CFU. In another embodiment, the effective amount administered is at least 25 micromolar [μM] in serum. In an embodiment, the effective concentration maintained is at least $10^5$ CFU and more preferably at least $10^8$ CFU. In another embodiment, the effective concentration maintained is at least 25 micromolar [μM] in serum.

In some embodiments, Nε-Methyl-L-lysine has a predetermined dose in a range of 0.0001-100 mg/g body weight to alter microbial composition of gut microbiota, to increase the number or relative abundance of total gut bacteria, to increase the number or relative abundance of total gut bacteria or the bacteria classified in the Actinobacteria phylum, Bacteroidia phylum, Verrucomicrobiota phylum, Bacilli class Coriobacteriia class, Saccharimonadia class, *Bifidobacterium* genus, and *Lactobacillus* genus.

Figure 11:
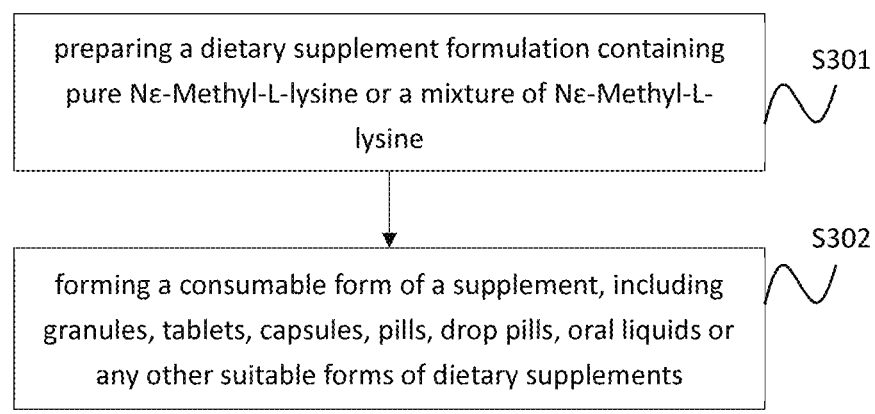
FIG. 11 illustrates a flow chart of the method for manufacturing dietary supplement for treating obesity, obesity-related diseases or cancers.

As shown in FIG. 11, it illustrates a flow chart of the method for manufacturing dietary supplement for treating obesity, obesity-related diseases or cancers. The method comprises: S301, preparing a dietary supplement formulation containing pure Nε-Methyl-L-lysine or a mixture of Nε-Methyl-L-lysine; and S302, forming a consumable form of a supplement, including granules, tablets, capsules, pills, drop pills, oral liquids or any other suitable forms of dietary supplements.

In some embodiments, Nε-Methyl-L-lysine has a predetermined dose in a range of 0.0001-100 mg/g body weight to increase the number of beneficial gut bacteria *Akkernmansia muciniphilla* in gut. In some embodiments, the above mentioned Nε-Methyl-L-lysine predetermined dose is in a range of 0.0001-0.0010 mg/g body weight. In some other embodiments, the above mentioned Nε-Methyl-L-lysine predetermined dose is in a range of 0.0011-0.0100 mg/g body weight. In some other embodiments, the above mentioned Nε-Methyl-L-lysine predetermined dose is in a range of 0.0110-0.100 mg/g body weight. In some other embodiments, the above mentioned Nε-Methyl-L-lysine predetermined dose is in a range of 0.1-1.000 mg/g body weight. In some other embodiments, the above mentioned Nε-Methyl-L-lysine predetermined dose is in a range of 1.1-10 mg/g body weight. In some other embodiments, the above mentioned Nε-Methyl-L-lysine predetermined dose is in a range of 10-100 mg/g body weight.

In some embodiments, the mixture of Nε-Methyl-L-lysine and L-lysine from ratio 1:1000000 to 1:1 is used Nε-Methyl-L-lysine.

In some embodiments, the mixture of Nε-Methyl-L-lysine and L-lysine from ratio 1:1000000 to 1:1 is used for dietary supplement or treating a subject with cancers in need of chemotherapy or immunotherapy.

In some embodiments, the mixture of Nε-Methyl-L-lysine and L-lysine from ratio 1:1000000 to 1:1 is used for dietary supplement or treating a subject in need of increasing the number or relative abundance of total gut bacteria, to increase the number or relative abundance of total gut bacteria or the bacteria classified in the Actinobacteria phylum, Bacteroidia phylum, Verrucomicrobiota phylum, Bacilli class Coriobacteriia class, Saccharimonadia class, *Bifidobacterium* genus, and *Lactobacillus* genus.

In some embodiments, the mixture of Nε-Methyl-L-lysine and L-lysine from ratio 1:1000000 to 1:1 is used for dietary supplement or treating a subject in need of increasing the number of beneficial gut bacteria *Akkernmansia muciniphilla* in gut.

In some embodiments, any probiotic is selected from the following group consisting of *Akkermansia muciniphila, Bifidobacterium bifidum, Bifidobacterium breve, Bifidobacterium longum* subsp. *infantis, Bifidobacterium longum, Lactobacillus acidophilus, Lactobacillus casei, Lactococcus lactis, Lactobacillus casei* subsp. *paracasei, Lactobacillus plantarum, Lactobacillus rhamnosus* and *Streptococcus thermophilus* to prepare the mixture with Nε-Methyl-L-lysine is used for treating the subject in need of treatment for obesity, obesity-related diseases, metabolic syndrome, type II diabetes, hypertension, cardiovascular disease, nonalcoholic fatty liver disease, nonalcoholic steatohepatitis, liver fibrosis and liver cirrhosis or cancers.

More embodiments are disclosed below: a method for manufacturing probiotic composition for treating obesity, obesity-related diseases or cancers, comprising: preparing a mixture comprising Nε-Methyl-L-lysine; and adding said mixture into probiotic. The method may further comprise a step of adding prebiotic into the mixture of Nε-Methyl-L-lysine, and preferably, the prebiotic is Inulin, Fructo-Oligosaccharide (FOS), Galacto-oligosaccharides (GOS), or amino acids.

The probiotic is selected from the group consisting of *Akkermansia muciniphila, Bifidobacterium bifidum, Bifidobacterium breve, Bifidobacterium longum* subsp. *infantis, Bifidobacterium longum, Lactobacillus acidophilus, Lactobacillus casei, Lactococcus lactis, Lactobacillus casei* subsp. *paracasei, Lactobacillus plantarum, Lactobacillus rhamnosus,* and *Streptococcus thermophilus.*

A method for regulating gut microbiota in a subject comprising: increasing either the amount of or the activity of a Nε-Methyl-L-lysine in the subject. A method of counteracting cancer-related immune suppression and restore effective antitumor immunity, comprising administering one or more of compositions including Nε-Methyl-L-lysine. A method of improving cancer survival rates, and quality of life, comprising administering one or more of compositions including Nε-Methyl-L-lysine. A method for manufacturing dietary supplement for treating obesity, obesity-related diseases or cancers, comprising: preparing a mixture comprising Nε-Methyl-L-lysine and L-lysine; and adding said mixture into food.

In one embodiment of the present disclosure, the amount of Nε-Methyl-L-lysine is an effective amount of Nε-Methyl-L-lysine/L-lysine mixture to the subject.

In one another embodiment of the present disclosure, the mixture of Nε-Methyl-L-lysine and L-lysine may be formed as granules, tablets, capsules, pills, drop pills, oral liquids, granules, particles, powders or any other suitable form of dietary supplement. In other embodiment, the dietary supplement may further comprises a package enclosing multiple edible containers.

With the above disclosure, it is proved that it is possible to treat obesity-related diseases or solid by increasing the amount of Nε-Methyl-L-lysine in the subject, or increasing the amount of the Nε-Methyl-L-lysine producing bacteria in the gut of the subject.

The description is presented to enable one of ordinary skill in the art to make and use the invention. Various modifications to the described embodiments are readily apparent to those persons skilled in the art and the generic principles herein can be applied to other embodiments. Thus, the present invention is not intended to be limited to the embodiments shown but is to be accorded the widest scope consistent with the principles and features described herein. It is readily apparent to one skilled in the art that other modifications can be made to the embodiments without departing from the spirit and scope of the invention as defined by the appended claims.

What is claimed is:

1. A method for treating obesity or obesity-related diseases comprising:
   a) diagnosing a subject in need of treatment for obesity, an obesity-related disease; and
   b) increasing an amount of Nε-Methyl-L-lysine in the subject by administering an effective amount of Nε-Methyl-L-lysine or Nε-Methyl-L-lysine hydrochloride based on the diagnosing to reduce a body mass index or a percentage of fat in a predetermined organ.

2. The method of claim 1, wherein the obesity-related diseases is selected from the group consisting of metabolic syndrome, type II diabetes, hypertension, cardiovascular disease, nonalcoholic fatty liver disease, nonalcoholic steatohepatitis, liver fibrosis and liver cirrhosis.

3. The method of claim 2, wherein the subject is selected from the group consisting of a human, a dog, a cat, a cow, a horse, a rabbit, a pig, a goat, an avian species and a fish species.

4. A method of reducing a fat percentage in an organ or a body comprising:
   a) altering a microbiota composition in the subject's gastrointestinal tract by administering an effective amount of Nε-Methyl-L-lysine, or Ne-Methyl-L-lysine hydrochloride; and
   b) maintaining an effective concentration of the Nε-Methyl-L-lysine or the Nε-Methyl-L-lysine hydrochloride in the subject's serum to reduce a fat percentage in the organ or the body.

5. The method of claim 4, wherein the effective amount administered is results in or produces at least 25 micromolar [μM] in serum.

6. The method of claim 4, wherein the effective concentration maintained is at least 25 micromolar [μM] in serum.

* * * * *